US009855353B1

(12) United States Patent
Stacy

(10) Patent No.: US 9,855,353 B1
(45) Date of Patent: Jan. 2, 2018

(54) RAPID DISINFECTION SYSTEM FOR AMBULANCE PATIENT CABIN

(71) Applicant: Brian Michael Stacy, Palm Harbor, FL (US)

(72) Inventor: Brian Michael Stacy, Palm Harbor, FL (US)

( * ) Notice: Subject to any disclaimer, the term of this patent is extended or adjusted under 35 U.S.C. 154(b) by 0 days.

(21) Appl. No.: 15/139,402

(22) Filed: Apr. 27, 2016

Related U.S. Application Data

(60) Provisional application No. 62/153,604, filed on Apr. 28, 2015.

(51) Int. Cl.
*A61L 2/24* (2006.01)
*A61L 2/10* (2006.01)
*B08B 7/00* (2006.01)
*G01J 1/42* (2006.01)

(52) U.S. Cl.
CPC ....... *A61L 2/10* (2013.01); *A61L 2/24* (2013.01); *B08B 7/0057* (2013.01); *G01J 1/429* (2013.01)

(58) Field of Classification Search
USPC .................................................. 250/455.11
See application file for complete search history.

(56) References Cited

U.S. PATENT DOCUMENTS

| 7,507,369 B2 * | 3/2009 | Lu ............................. A61L 2/04 219/679 |
| 8,114,346 B2 * | 2/2012 | Hyde ......................... A61L 2/10 250/492.1 |
| 2012/0100040 A1 * | 4/2012 | Andersen ............... A01N 41/10 422/28 |
| 2015/0190538 A1 * | 7/2015 | Olvera ....................... A61L 2/22 422/107 |
| 2016/0000951 A1 * | 1/2016 | Kreiner .................. A61L 2/0047 422/24 |

FOREIGN PATENT DOCUMENTS

CN          203703782 U  *  7/2014  .............. F21S 8/10

OTHER PUBLICATIONS

Kowalski, "Ultraviolet Germicidal Irradiation Handbook", Springer (2009), pp. 7-8.*

* cited by examiner

*Primary Examiner* — Phillip A Johnston

(57) ABSTRACT

Rapid Disinfection System that is able to disinfect the surfaces of a Rescue Ambulance Patient Cabin after all necessary hand disinfection protocols have been completed. As with emergency situations timing is critical. This system can disinfect the patient cabin rapidly within minutes with very little operator effort. This will allow for little to no down time of the rescue ambulance. Larger populated areas may have as much as 50,000 emergency calls in a months' time and may only have 20 to 30 rescue ambulance to handle all of these calls. In these areas there may only be less than 5 minutes surface disinfection times available.

18 Claims, 21 Drawing Sheets

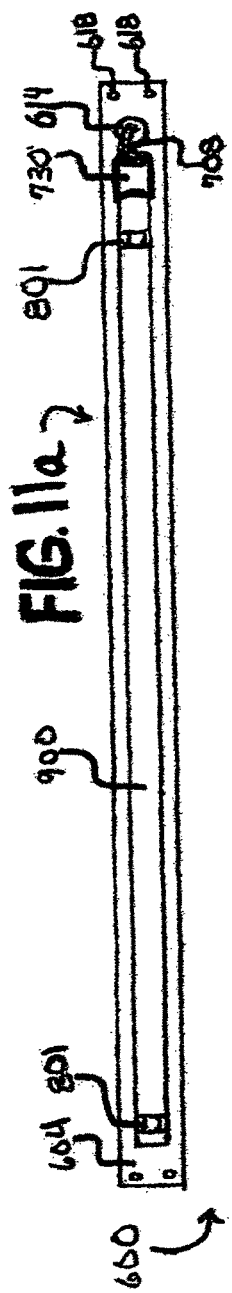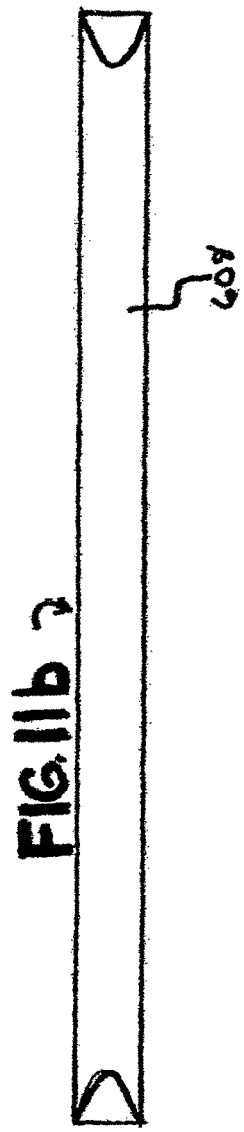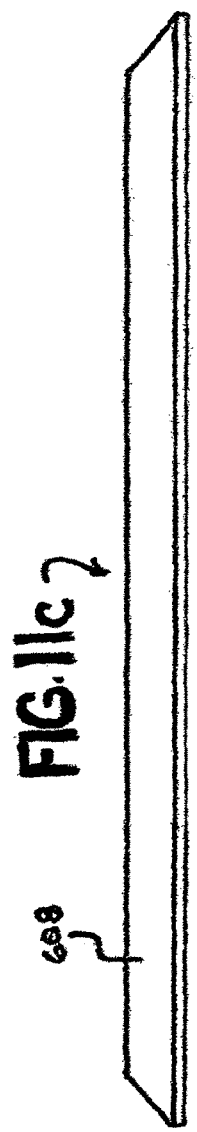

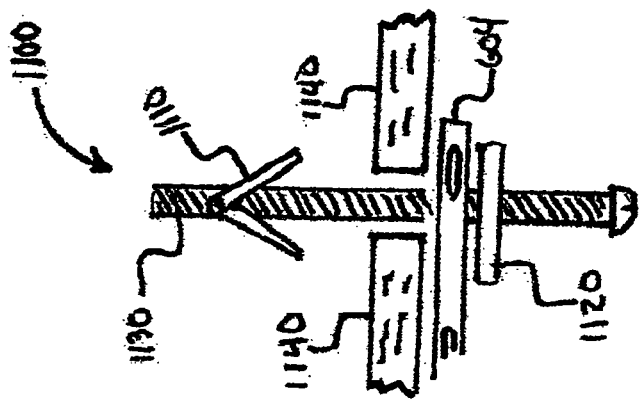
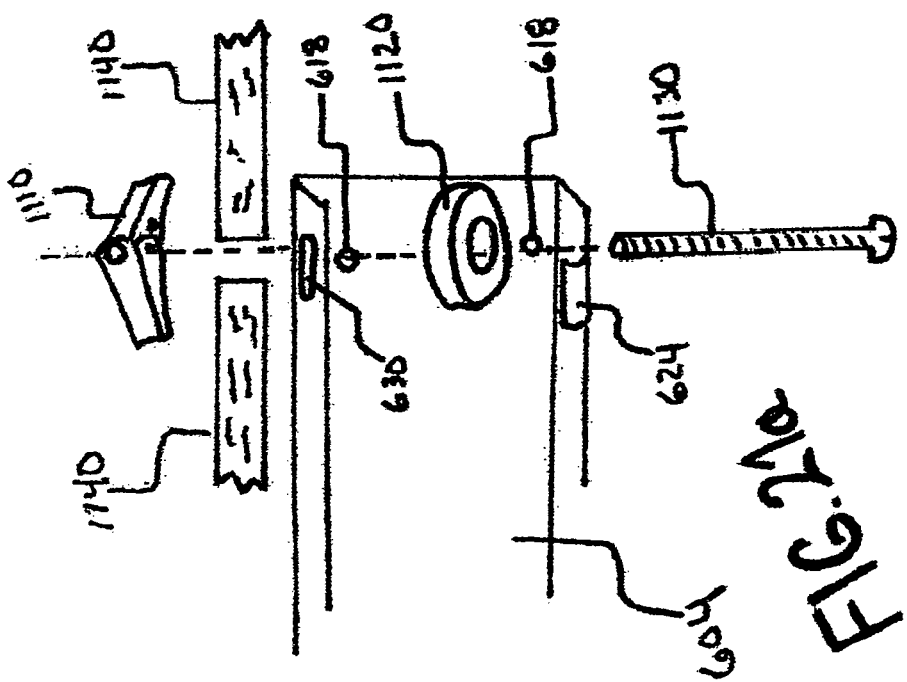

RAPID DISINFECTION SYSTEM FOR AMBULANCE PATIENT CABIN

CROSS-REFERENCE TO RELATED APPLICATIONS

This application claims priority to U.S. Provisional patent application Ser. No. 62/153,604, filed Apr. 28, 2015, the entire contents of which are hereby incorporated by reference.

FIELD OF THE INVENTION

The present invention relates to a system for rapid disinfection of surfaces in rescue ambulance patient cabins where time is limited and related methods thereof and, more particularly, to ultraviolet-C band surface disinfection.

BACKGROUND OF INVENTION

Healthcare acquired infections; pandemic events and bioterrorist event are of growing concerns and have become a consistent drain on healthcare related funds. The list of multi drug resistant microorganisms are growing and becoming a threat to the population around the world. Healthcare related secondary infections are most commonly associated with medical facilities such as hospitals.

Hand disinfection protocols have been in place for many years and have limited success in effective surface disinfection. This method of disinfecting surfaces relies on chemicals and can take extended periods of time based on the need for saturation of surfaces to be disinfected and extended drying times need for the chemicals used.

Surface disinfection using Ultraviolet-C band lighting is considered ultraviolet germicidal irradiation or UVGI. This disinfection method using ultraviolet-C band short wave 254 nanometer light waves inactivates or kills microorganisms at the cellular level by destroying the nucleic acids and disrupting their DNA or RNA. This process will render the organisms incapable of reproducing, therefor killing the microorganism. This process prevents the microorganism from multiplying and thereby stopping the microorganism from causing infections.

Some basic advantages with using an Ultraviolet germicidal irradiation UVGI system are no chemicals used, no chemical storage needed, and no remaining residue clean up from chemical use along with no chemical odors. An Ultraviolet germicidal irradiation UVGI system can reduce the cost of employee hours as it requires very little operating effort to achieve the intended results. The element of human error is kept to a very minimum risk factor as the ultraviolet germicidal irradiation UVGI system will produce the same results each time as there is no variance of effort in the surface disinfection of the ultraviolet-C band lamp.

Special caution must be taken while operating an ultraviolet germicidal irradiation UVGI system. Handling any type of mobile unit ultraviolet germicidal irradiation UVGI system comes with risk as set up of system and take down can subject the employee to hazards related to breakage or burns from hot lamps. As with any piece of equipment that is mobile there is a need for space to store when not in use.

As with any lamp they are made of glass and should be handled with care when replacing. Exposure to ultraviolet-C band light waves can be harmful to skin and eyes. Strict calculations must be adhered to when determining the specific location for the installation of the ultraviolet-C band lamp to minimize or eliminate shadowing.

As described above, it is necessary to pay close attention to the special cautions when designing a system that incorporates ultraviolet-C band lamps for surface disinfection. However the advantages over chemical processes are numerous and make the use of ultraviolet-C band lamps for surface disinfection a necessary and highly effective tool in the fight against microorganisms in rescue ambulance patient cabins. Once a Rapid Disinfection System using ultraviolet-C band lamps for surface disinfection is installed within the rescue ambulance patient cabin there is no need for storing equipment or man power to set up and remove the disinfection equipment. There is a need for a system to disinfect the surfaces of a rescue ambulance patient cabin within the shortest amount of time but also limit employee risk. There needs to be the ability to utilize system at any time without delays from set up of equipment and take down once irradiation phase is complete. Yet another critical necessity is to have the ability to disinfect the surfaces of the rescue ambulance patient cabin parked in the emergency service building or if the need arises out in the field responding to an emergency call.

The Rapid Disinfection System described herein these specifications is intended to deliver at least a three log reduction of colony forming units of microorganisms on surfaces or airborne within the Rescue Ambulance Patient Cabin. The targeted microorganisms would include but are not limited to *Clostridium Difficile* (C-Diff), Methicillin-Resistant *Staphylococcus Aureus* (MRSA), and Influenza. These results must be achieved rapidly within only a few minutes or less. This time frame is based on the nature of rescue emergencies. The Rescue Ambulance needs to be ready to travel to the emergency call site quickly. There may not be a lengthy time to use equipment that takes 30 minutes to 90 minutes to set up, Irradiate and take down. This is based on current time frames of portable UVC units currently use in Hospital and Rescue Ambulance settings.

The said system is designed to be operated by any first responder with limited training. In other words the system power switch is unlocked and turned on. This is the power timer switch that will energize the lamps and all safety protocols incorporated within the Rapid Disinfection System. The same power timer switch will then turn off or shut down the entire system at the end of the calculated time frame.

The UV lamps will need to irradiate the interior of the Rescue Ambulance Patient Cabin for a calculated time frame in order to achieve the appropriate measured UV dosage.

In order to achieve the desired three log reduction or better of CFU's of microorganisms in the Rescue Ambulance Patient Cabin, a measured UV dose of 46,000 microwatts is necessary based on (Ref #1)

(Ref #1) In a published study by Moog Life Sciences Laboratories dated May 2012 *Clostridium difficile* Spore Inactivation Study Using Ultraviolet-C Energy, showed that a 3.4 log reduction of CFU of C-Diff was achieved with a measured UV dosage of 45,903 microwatts

SUMMARY OF THE INVENTION

One facet of the present invention provides a complete ultraviolet-C band germicidal disinfection system for rescue ambulance patient cabin surfaces. A plurality of Independent high output ultraviolet-C band lamps are mounted to the ceiling of the patient cabin strategically to minimize shadowing to achieve optimal surface disinfection of the patient cabin.

Another facet of the present invention provides a reflective hard surface mounting fixture design that enhances the ultraviolet-C band irradiance intensity due to the reflective properties. In one embodiment the reflective hard surface mounting fixture comprises of the ability to be securely fastened to the ceiling panels of the patient cabin. Additionally the reflective hard surface mounting fixture is incorporates a cover that locks tightly to the base portion to protect the said lamp from breakage.

In another preferred embodiment, the reflective hard surface fixture comprises of lamp mounting clips with rubber grommet, designed to securely lock in place the high output ultraviolet-C band lamps. The lamp clip and rubber grommet will protect the hard quartz glass tubes of the ultraviolet-C band lamp from shifting or dislodging from the reflective hard surface fixture as a result of G force that occurs from rescue ambulance hitting bumps on or off the road.

In another preferred embodiment, is a protective coating derived from a Teflon tube placed over the glass portion of the ultraviolet-C band lamp. This protective coating will contain any broken glass shards or any mercury vapor leak in the event the ultraviolet-C band lamp breaks.

In another preferred embodiment, special ultraviolet-C band light wave resistant lamp cords are used. Ultraviolet-C band light waves can overtime destroy plastic or rubber insulation on electrical wires. In another preferred embodiment, the ultraviolet-C band light wave resistant lamp cords have a water tight locking four pin connection. This four pin connection is exclusive to the rapid disinfection system only allowing for high output ultraviolet-C band germicidal lamps to operate with the high output milliamp power supply.

Another facet of the present invention provides a rapid disinfection system that will minimize or eliminate accidental human exposure of ultraviolet-C band light wave during surface disinfection phase. Exposure to ultraviolet-C band light waves can be harmful to eyes and skin if subject to direct exposure. Human occupancy of the rescue ambulance patient cabin is strictly prohibited.

In another preferred embodiment, the rapid disinfection system comprises of hard wired infrared motion and heat sensor located within the rescue ambulance patient cabin to detect any motion. If any motion is detected within the patient cabin by the hard wired infrared motion and heat sensor all electrical current will be completely disconnected immediately from rapid disinfection system during the surface disinfection phase thus shutting of high output ultraviolet-C band lamps.

In another preferred embodiment, the rapid disinfection system comprises of two part hard wired door interlock safety switches installed on each entry door and door frame as to make a circuit connection. When door is closed tight and latched within the rescue ambulance patient cabin the electrical circuit is complete and power will run to energize the high output ultraviolet-C band lamps for the surface disinfection phase. If any of the doors are ajar or in the unlatched position, the two part hard wired two part hard wired door interlock switches will disconnect electrical current from rapid disinfection system during the surface disinfection phase thus shutting of high output ultraviolet-C band lamps.

In another preferred embodiment, the rapid disinfection system comprises of ultraviolet-C band safety feature capable of sending warning notice of unsafe ultraviolet-C band irradiance intensity levels. Ultraviolet-C band germicidal irradiance levels degrade over the life of the lamp rendering the ultraviolet-C band lamp ineffective. Said ultraviolet-C band germicidal irradiance Intensity monitor will be able to determine the ultraviolet-C band intensity output of the ultraviolet-C band lamp.

Another facet of the present invention provides an alternating current (AC) direct current (DC) power inverter will allow the Rapid Disinfection System to operate while the rescue ambulance is in motion and not connected to a shoreline power source, the rescue ambulance may energize the Rapid Disinfection System while on the roadways.

In another preferred embodiment, the alternating current (AC) direct current (DC) power inverter will be in direct line to at least the 12 volt or 24 volt battery or string of batteries located in the rescue unit. Said power inverter will transform the 12 volts or 24 volts to the 120 line voltage needed to energize the Rapid Disinfection System when disconnected from the 120 line volt shoreline power connection available in the emergency services rescue station garage or any standing power stations producing 120 line volt power.

Another facet of the present invention provides a preset multifunction timer switches to energize the high output ultraviolet-C band lamps located in the rescue ambulance patient cabin for surface disinfection.

Another facet of the present invention provides a data collection system that comprises of a module to receive incoming data points from the components to the rapid disinfection system. Another preferred embodiment, of the data collection system is the ability to disseminate the data and dispatch this collected information to a manned monitoring station. The collected data will give historical information of system use, critical safety feature and ultraviolet-C band irradiance intensity levels in real time whether it is to a device located in the driver cabin of the rescue ambulance or in the emergency service building location or remote view for technical service report from the manufacturer.

BRIEF DESCRIPTION OF THE DRAWINGS

FIG. 11a is a perspective view of the reflective hard surface UVC Lamp mounting fixture base portion of the present invention;

FIG. 11b is a perspective view of the reflective hard surface UVC Lamp mounting fixture safety cover of the present invention (Top View);

FIG. 11c is a perspective view of the reflective hard surface UVC Lamp mounting fixture safety cover of the present invention (Side View Length);

FIG. 11d is a perspective view of the reflective hard surface UVC Lamp mounting fixture safety cover of the present invention (Side View End);

FIG. 21a is a exploded perspective view of the vibration resistant mounting bolt assembly of the present invention;

FIG. 21b is a perspective view of vibration resistant mounting bolt assembly of the present invention.

DETAILED DESCRIPTION OF THE INVENTION

Figure 1:
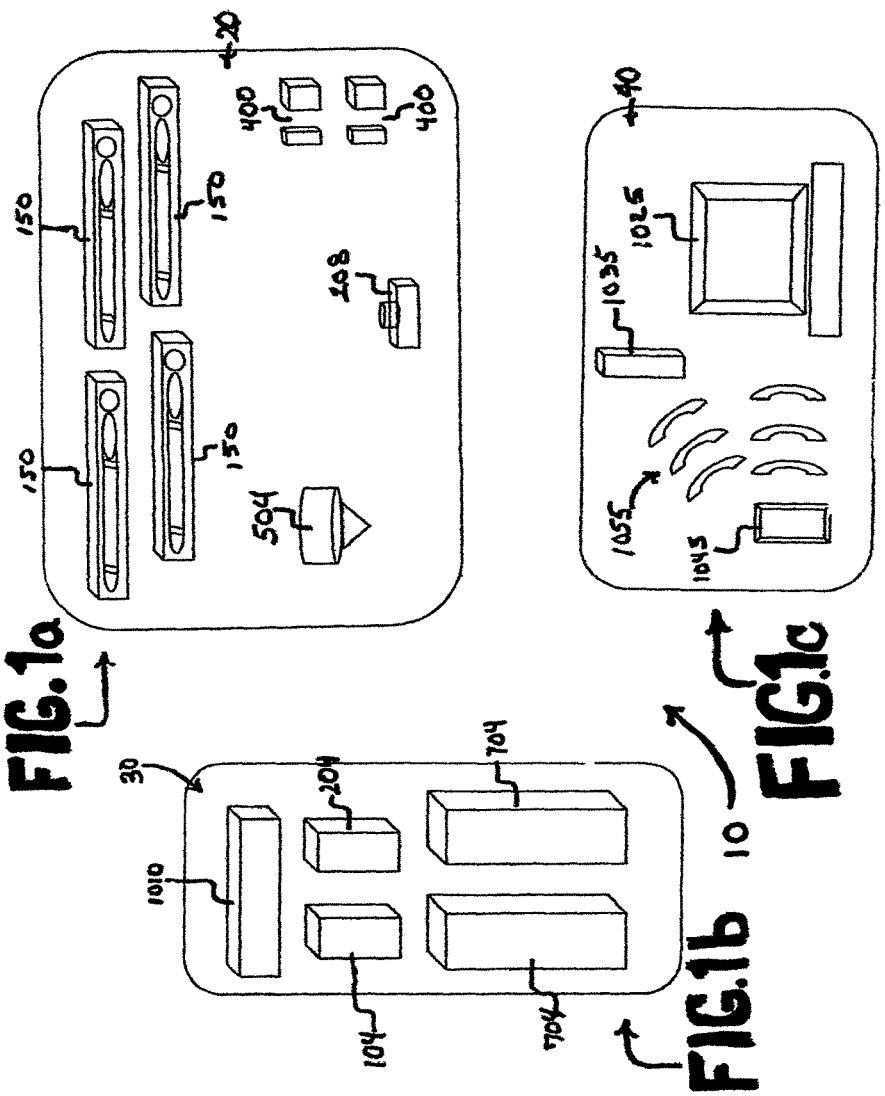
FIG. 1a is a perspective view of an embodiment of a system of the present invention.
FIG. 1b is a perspective view of an embodiment of a system of the present invention.
FIG. 1c is a perspective view of an embodiment of a system of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring now to the figures and first to FIG. 1a, FIG. 1b and FIG. 1c there is shown an embodiment of a Rapid Disinfection System 10 of the present invention. Rapid Disinfection System FIG. 1a generally includes items located within the rescue ambulance patient cabin as follows, but not limited to four high output UVC lamps with reflective hard surface mounting fixtures 150 mounted to the ceiling; hard wired infrared motion sensor 504 affixed high up a wall or to the ceiling to have more of a complete view of the patient cabin to detect motion and or heat, 360 degree UVC irradiance intensity sensor 208 mounted in a lower position in the rescue cabin to detect the UVC light waves for monitoring and two part door interlock switches 400 mounted on all entry doors to the rescue cabin. Generally all of said devices will be connected to the data collection terminal 1045 (shown in FIG. 1c) for reporting of all data.

Rapid Disinfection System FIG. 1b generally includes items located in an exterior cabinet of the rescue ambulance as follows; but not limited to Alternating Current (AC) Direct Current (DC) power inverter 1010, preset multifunction timer switch with manual override timer and auto shut off capabilities 104, ultraviolet-C band irradiance Intensity monitor 204, and high output milliamp power supplies 704. Each of the said components may be mounted within the locking NEMA 4 weather tight cabinet 304 (shown in FIGS. 8a and 8b) that will be mounted within the exterior cabinet of the rescue unit. Generally all of said devices will be connected to the data collection terminal 1045 (shown in FIG. 1c) for reporting of all data.

Figure 4:
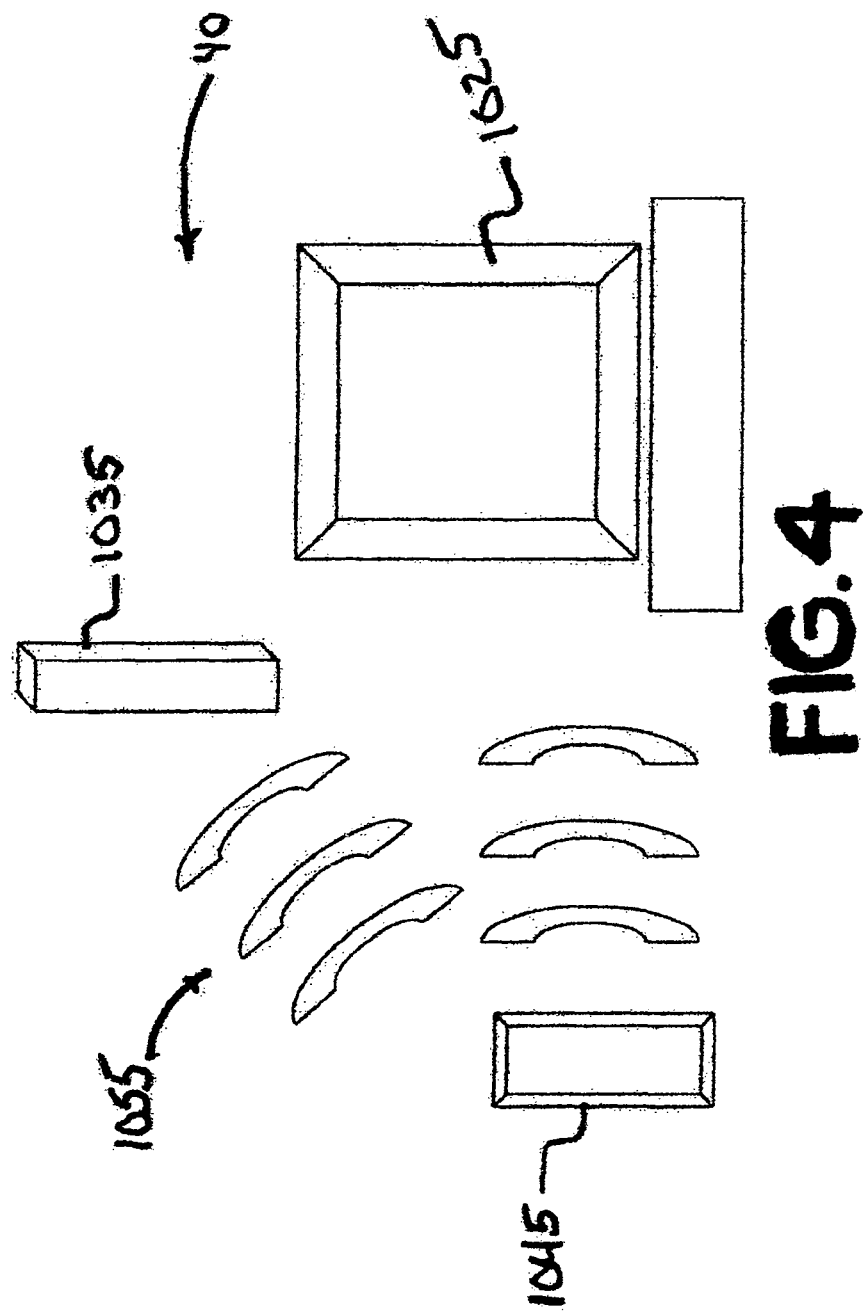
FIG. 4 is a perspective view of an embodiment of a system of the present invention.

Rapid Disinfection System FIG. 1c generally includes items located in a remote location such as but not limited to a computer terminal 1025, and mobile device 1035. A data collection terminal 1045 may be installed within the rescue ambulance exterior cabinet. Said device would be connected to generally all of the individual devices within Rapid Disinfection System FIG. 1a also shown in FIG. 2. A data collection terminal 1045 would utilize the following means; radio waves, WIFI, blue tooth or hard wired data cable 1055 to receive and transfer all data collected to the remote manned monitoring stations as shown in FIG. 4. These means generally include but are not limited to wireless internet, blue tooth signaling, or hard wired tethered cable connection.

Figure 2:
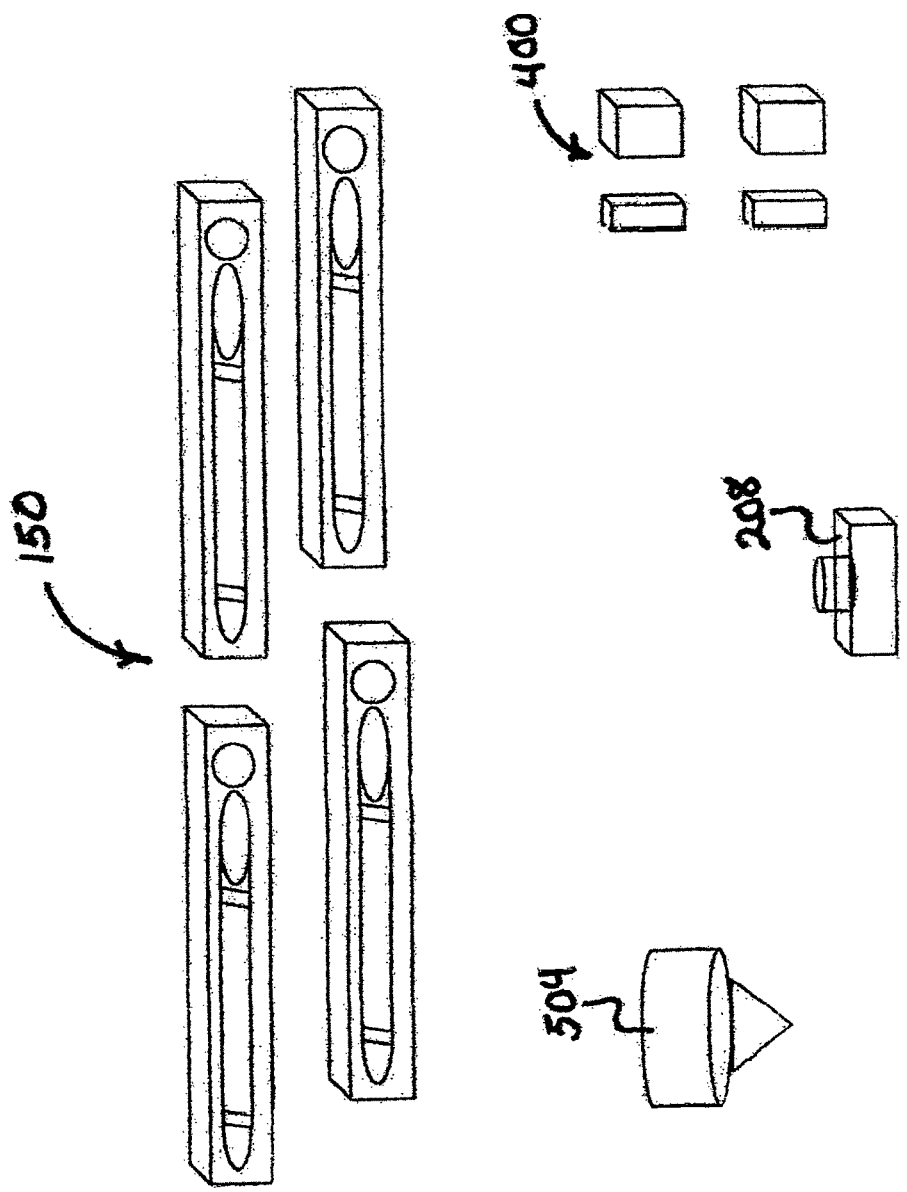
FIG. 2 is a perspective view of an embodiment of a system of the present invention.

Alternatively shown in FIG. 2 is an embodiment of Rapid Disinfection System 10 generally include but are not limited to a plurality of high output UVC lamps with reflective hard surface mounting fixtures 150 mounted to the ceiling; hard wired infrared motion sensor 504 affixed high up a wall or to the ceiling to have more of a complete view of the patient cabin to detect motion and or heat, 360 degree UVC irradiance intensity sensor 208 mounted in a lower position in the rescue cabin to detect the UVC light waves for monitoring and two part door interlock switches 400 mounted on all entry doors to the rescue cabin. Generally all of said devices will be connected to the data collection terminal 1045 for reporting of all data.

Figure 3:
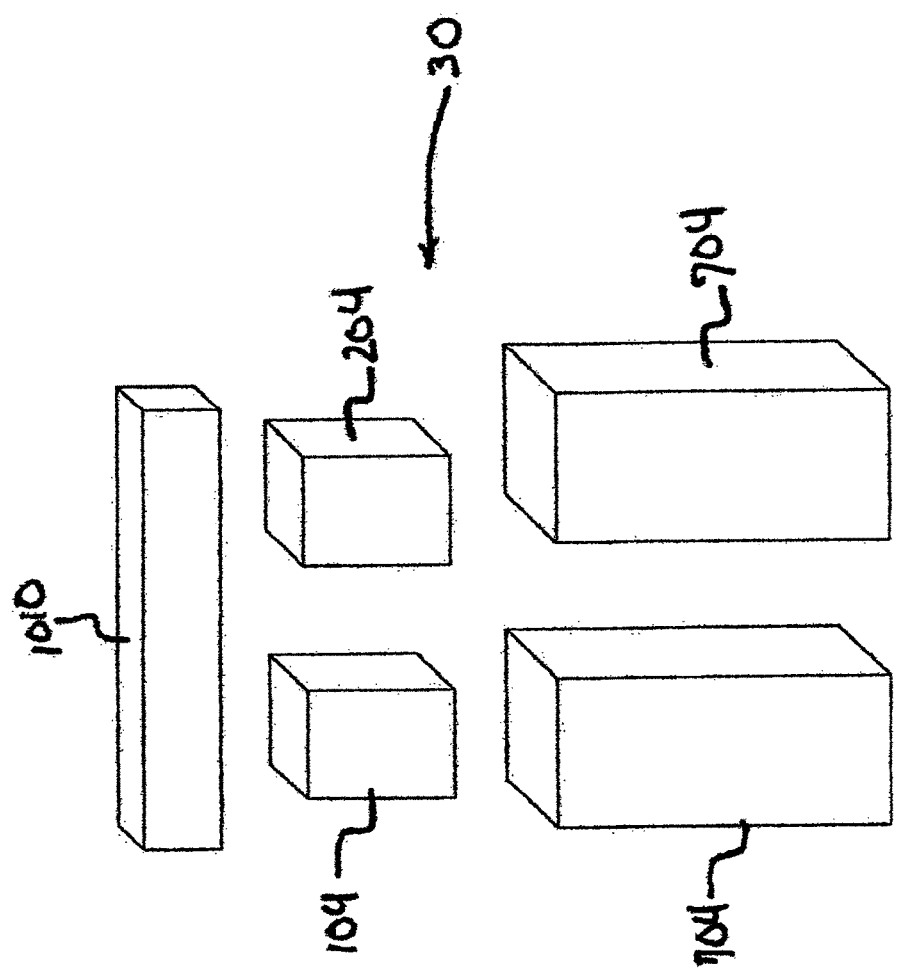
FIG. 3 is a perspective view of an embodiment of a system of the present invention.

Alternatively shown in FIG. 3 is an embodiment of Rapid Disinfection System 10 generally include but are not limited to Alternating Current (AC) Direct Current (DC) power inverter 1010, preset multifunction timer switch with manual override timer and auto shut off capabilities 104, ultraviolet-C band irradiance Intensity monitor 204, and high output milliamp power supplies 704. Each of the said components may be mounted within the locking NEMA 4 weather tight cabinet 304 (shown in FIG. 8a) that will be mounted within the exterior cabinet of the rescue unit. Generally all of said devices will be connected to the data collection terminal 1045 (shown in FIG. 4) for reporting of all data.

Alternatively shown in FIG. 4 is an embodiment of Rapid Disinfection System 10 generally include but are not limited to a computer terminal 1025, and mobile device 1035. A data collection terminal 1045 may be installed within the rescue ambulance exterior cabinet. Said device would be connected to generally all of the individual devices within Rapid Disinfection System 20 shown in FIG. 2. A data collection terminal 1045 would utilize the following means to receive and transfer all data collected to the remote manned monitoring stations as shown in FIG. 4. These means generally include but are not limited to wireless internet, blue tooth signaling, or hard wired tethered cable connection 1055.

Figure 5:
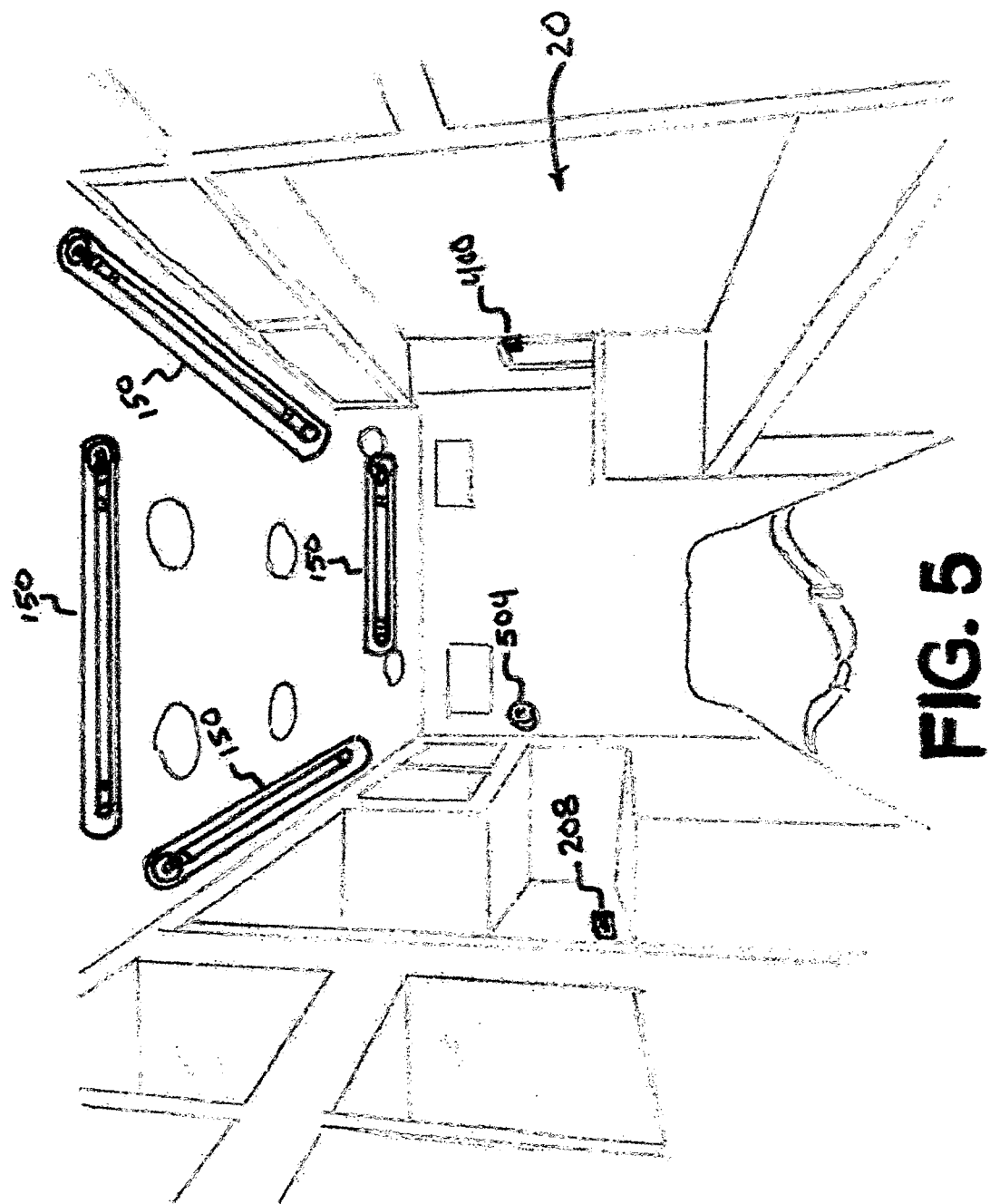
FIG. 5 is a perspective view of an embodiment of a system of the present invention.

Alternatively shown in FIG. 5 is an embodiment of Rapid Disinfection System 10 generally include but are not limited to showing the approximate installation locations for the Rapid Disinfection System 20. Parts are located within the rescue ambulance patient cabin. four high output UVC lamps with reflective hard surface mounting fixtures 150 mounted to the ceiling; hard wired infrared motion sensor 504 affixed high up a wall or to the ceiling to have more of a complete view of the patient cabin to detect motion and or heat, 360 degree UVC irradiance intensity sensor 208 mounted in a lower position in the rescue cabin to detect the UVC light waves for monitoring and two part door interlock switches 400 mounted on all entry doors to the rescue cabin. Generally all of said devices will be connected to the data collection terminal 1045 (shown in FIG. 4) for reporting of all data.

Figure 6:
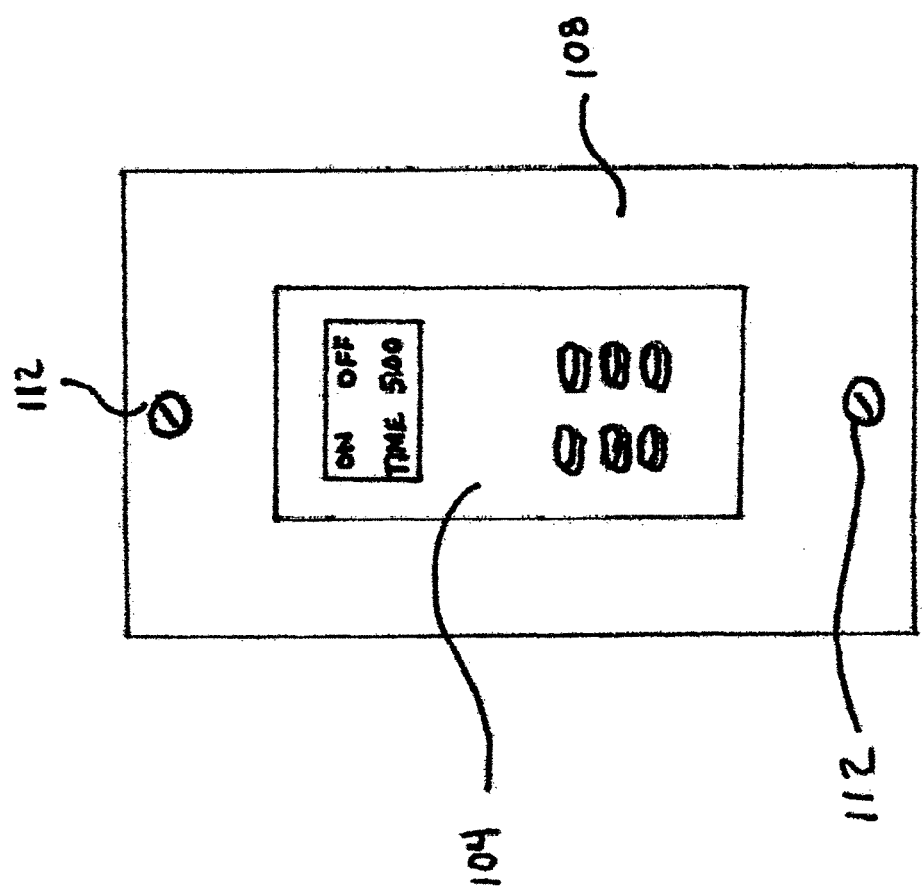
FIG. 6 is a perspective view of the preset multifunction timer switch with manual override timer and auto shut off capabilities of the present invention.

FIG. 6 shows one embodiment of the Rapid Disinfection System 10 preset multifunction timer switch with manual override timer and auto shut off capabilities 104. Said device 104 is utilized to program the appropriate time needed to disinfect the rescue ambulance patient cabin. Said device 104 has the capabilities to have multiple preset times for a variety of disinfection times. The said device 104 will also allow for manual override of programmed times when necessary. This device 104 will allow for all device of the Rapid Disinfection System to receive income power to operate. There is a flat cover plate 108 setting flush with the front of preset multifunction timer switch with manual override timer and auto shut off capabilities 104. The flat cover plate 108 will allow the said device 104 to be securely mounted with the screw mounting holes 112 located at the top and bottom of the flat cover plate 108 within the locking NEMA 4 weather tight cabinet 304 (shown in FIG. 8*a*) in the exterior compartment of the rescue ambulance. Said device 104 will be connected to the data collection terminal 1045 (shown in FIG. 4) for reporting of all data.

Figure 7:
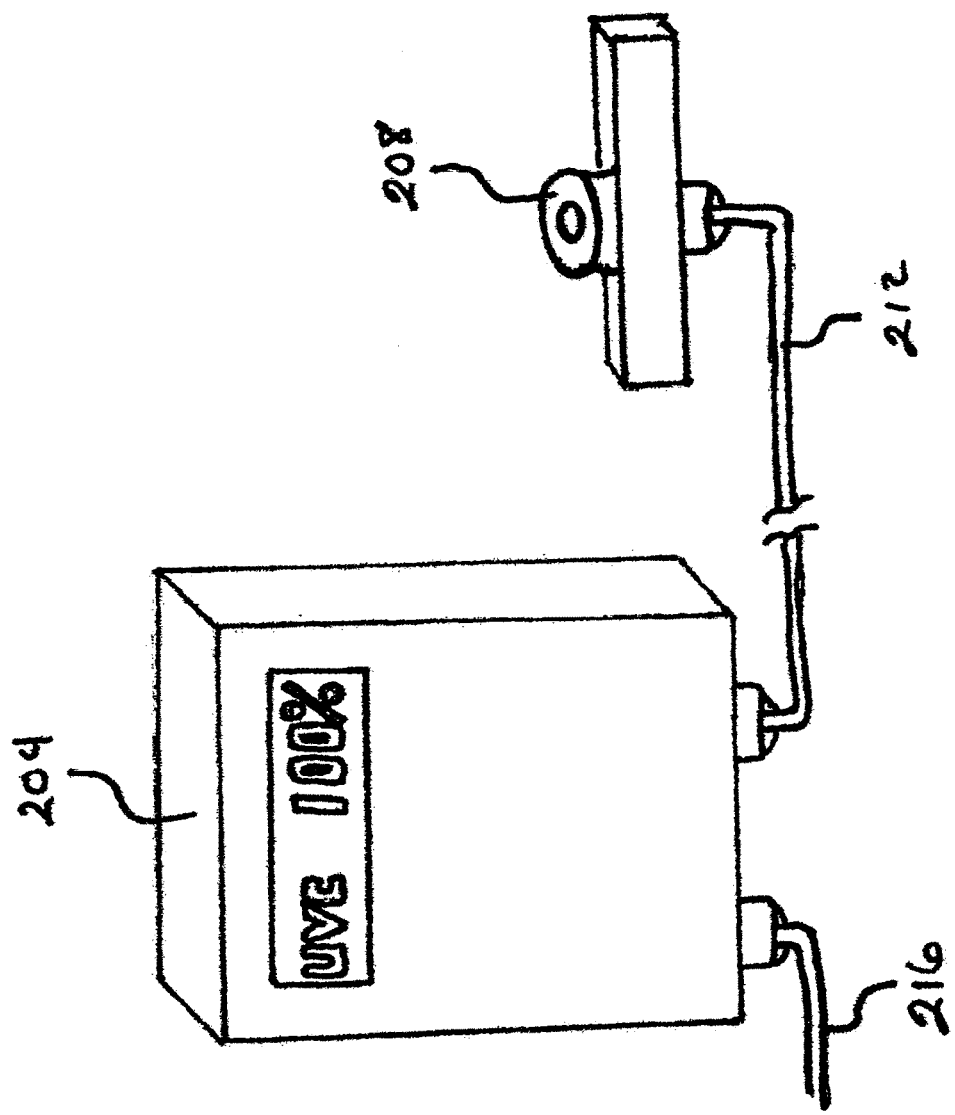
FIG. 7 is a perspective view of the ultraviolet-C band irradiance Intensity monitor with a 360 degree UV sensor of the present invention.

FIG. 7 shows one embodiment of the Rapid Disinfection System 10 ultraviolet-C band irradiance Intensity monitor 204 with a 360 degree sensor 208. Said device 204 will monitor the total ultraviolet-C band irradiance Intensity output from the high output ultraviolet-C band lamps 900 (shown in FIG. 15) located within the rescue ambulance patient cabin. Said device 204 will be located and mounted within the locking NEMA 4 weather tight cabinet 304 (shown in FIG. 8*a*) located within the exterior cabinet of the rescue ambulance. Said device 208 will be mounted within the patient cabin of the rescue unit and hard wired back to the device 204. Said 360 degree sensor 208 will be located in an area to allow full view of generally all of the high output ultraviolet-C band lamps 900 (shown in FIG. 15) to receive the UVC light wave intensity to be monitored. Said device 204 will be connected to the data collection terminal 1045 (shown in FIG. 4) for reporting of all data.

Figure 8:
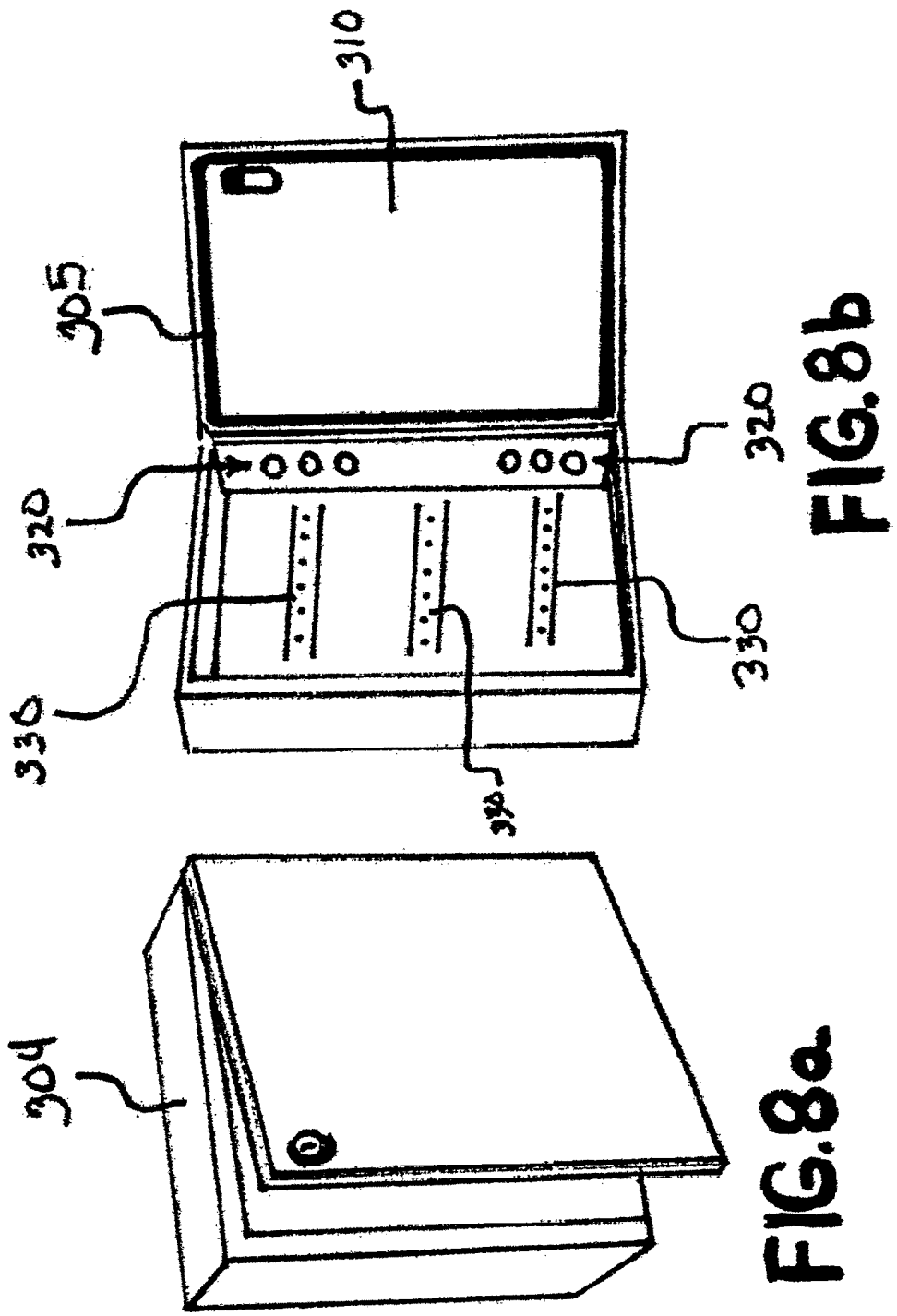
FIG. 8a is a perspective view of the locking NEMA 4 weather tight cabinet with door closed of the present invention.
FIG. 8b is a perspective view of the locking NEMA 4 weather tight cabinet internal hardware with door open of the present invention.

FIG. 8 shows one embodiment of the Rapid Disinfection System 10 locking NEMA 4 weather tight cabinet 304. Said device is manufactured using a hard material such as metal or plastic that can withstand high impact. This is necessary in order to protect the electrical devices mounted within. Generally all locking NEMA 4 weather tight cabinet 304 are weather tight and do not allow for any water intrusion with the aid of a rubber seal 305 affixed to the cabinet door 310. The interior of said cabinet 304 would generally include precut knock out openings 320 for the insertion of electrical wire. These said openings 320 can be removed based on need or may remain in place not allowing any water intrusion. Along the back panel of the cabinet 304 generally is mounting brackets with screw holes 330 for mounting of the electrical devices.

Figure 9:
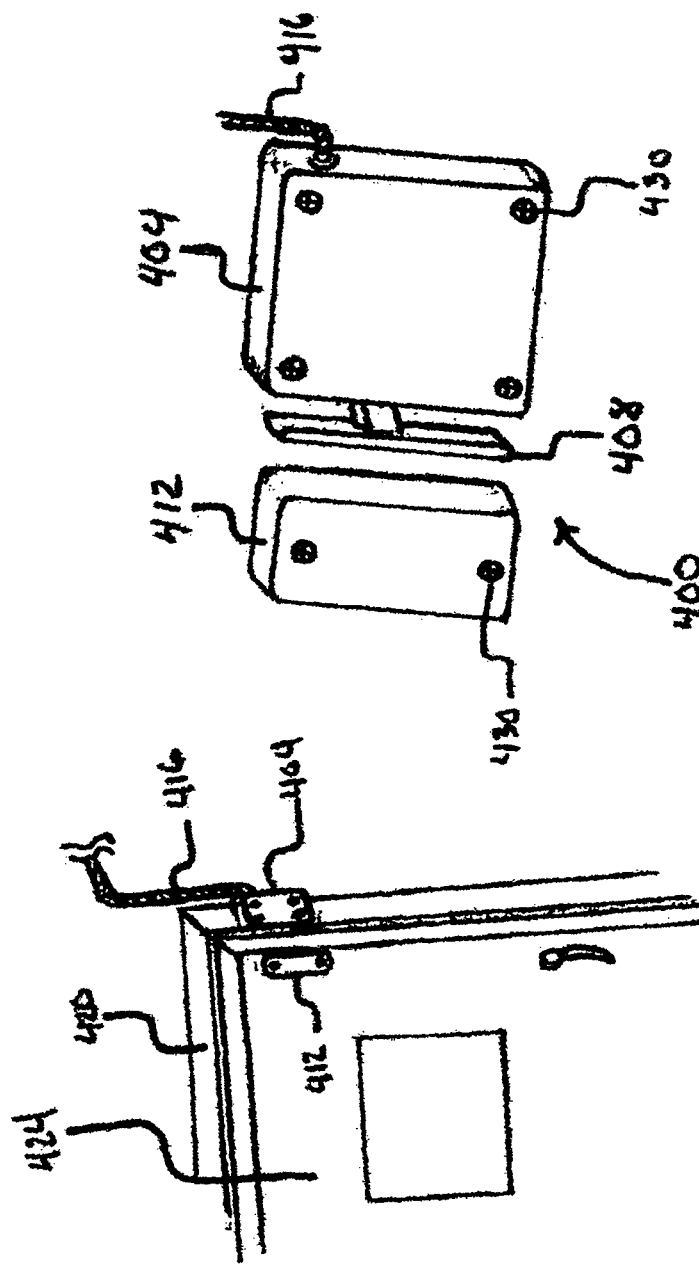
FIG. 9a is a perspective view of the two part hard wired door interlock switches installed on door and frame of the present invention.
FIG. 9b is a perspective view of the two part hard wired door interlock switches of the present invention.

FIG. 9 shows one embodiment of the Rapid Disinfection System 10 locking two part hard wired 416 door interlock switches 400. Door interlock switches generally come with a normally on switch pattern. This will allow for the electrical current to keep flowing to the lamps 900 (shown in FIG. 15). The two part switch is mounted with the hard wired 416 switch 404 mounted on the door frame 420. The pressure plate 412 is generally mounted to the face of the door 424. Once the door is opened and the pressure plate 412 is moved away from the hard wired 416 switch 404 located on the door frame this will allow for the moving arm 408 to extend and therefor break or open the normally on terminal and will stop the flow of electricity to the lamps 900 (shown in FIG. 15). Said device 400 will be connected to the data collection terminal 1045 (shown in FIG. FIG. 4) for reporting of all data.

Figure 10:
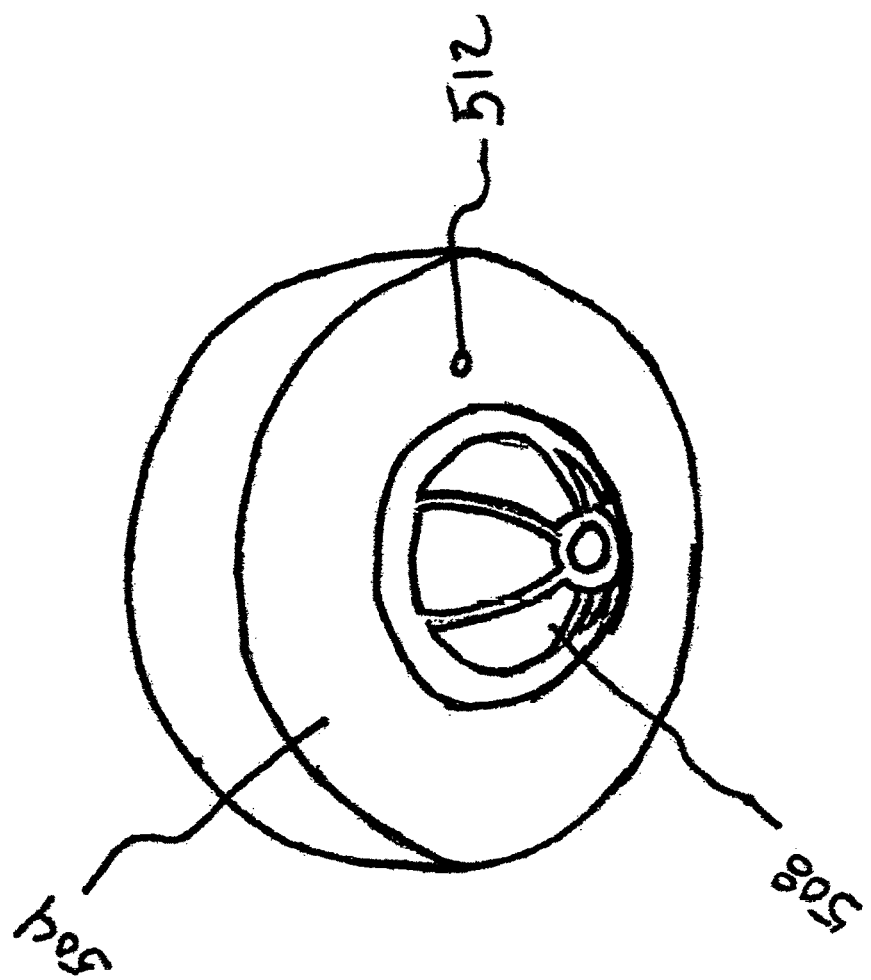
FIG. 10 is a perspective view of the hard wired infrared motion sensor of the present invention.

FIG. 10 shows one embodiment of the Rapid Disinfection System 10 hard wired infrared motion sensor 504. Generally one or more hard wired infrared motion sensor 504 will be mounted within the patient cabin of the rescue unit. This is to prevent any accidental human exposure. Said device 504 is generally used to detect any motion from an infrared motion sensor 508 and also may detect body heat via heat sensor 512. This device 504 is generally mounted in a location that would not be obstructed by any items in the patient cabin. Generally this device 504 would be installed on the ceiling or at the top of the walls. Said device 504 will be connected to the data collection terminal 1045 (shown in FIG. 4) for reporting of all data.

FIG. 11*a* shows one embodiment of the Rapid Disinfection System 10 reflective hard surface UVC Lamp mounting fixture in total as 600. Said fixture 600 consists of generally a reflective hard surface base portion of fixture 604. The reflective hard surface base portion of fixture 604 generally consist of as many as four mounting holes 618 located generally at the outer ends of the said base fixture portion 604. Generally located at one end of said base fixture 604 is at least one larger round lamp cord access opening 614 in which the ultraviolet-C band resistant lamp cords 708 (shown in FIG. 12) may be run up in to the ceiling to make a connection with the high output milliamp power supplies 704 (shown in FIG. 12) located in an exterior cabinet of the rescue ambulance.

FIG. 11*b* shows a reflective hard surface fixture safety cover 608. This is a view from top down. In addition to the said base portion 604 is the reflective hard surface fixture safety cover 608. Said safety cover 608 will lock in to place covering the entire said base portion 604 and therefore conceal the high output ultraviolet-C band lamps 900 (shown in FIG. 15) and ultraviolet-C band resistant lamp cords 708 (shown in FIG. 12). In this application the said device 900 (shown in FIG. 15) will be connected to the data collection terminal 1045 (shown in FIG. 4) for reporting of all data.

FIG. 11*c* shows a reflective hard surface fixture safety cover 608. This is a view from the side length wise.

FIG. 11d shows a reflective hard surface fixture safety cover 608. This is a view of the end cap.

Figure 12:
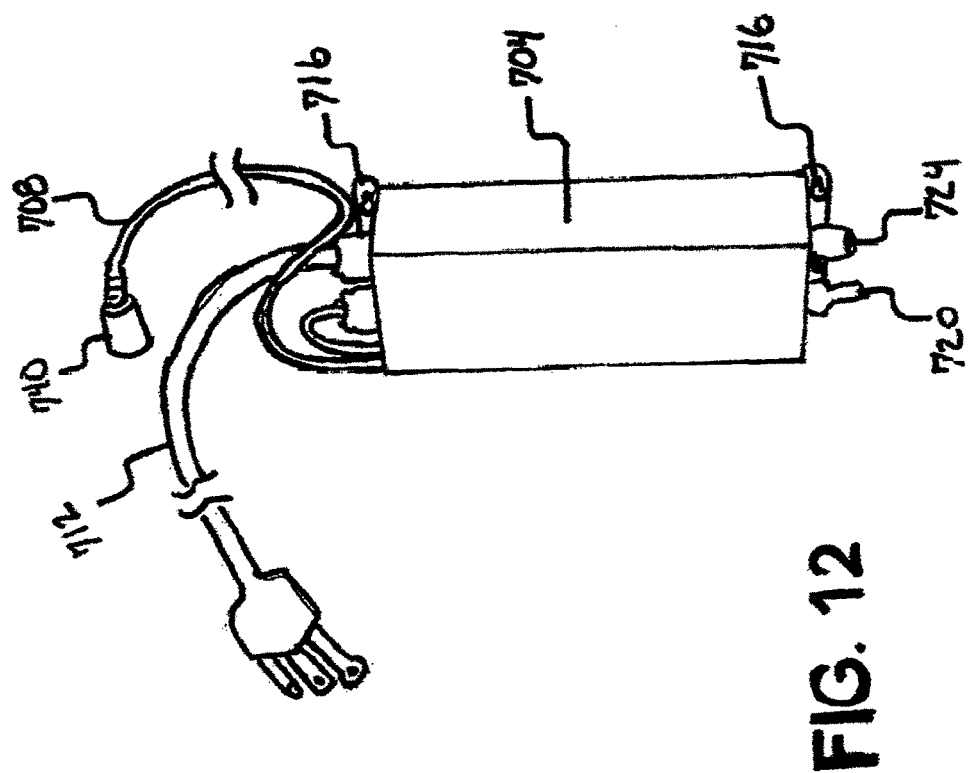
FIG. 12 is a perspective view of the high output milliamp power supplies of the present invention.

FIG. 12 shows one embodiment of the Rapid Disinfection System 10 high output milliamp power supplies 704. Said device 704 generally consist of internal high output milliamp power supply 704; one electrical power cord 712 to plug in to an electrical outlet. In addition to this there is one (on and off) safety switch 720 and one 20 amp fuse 724 located inside a weather tight housing. In addition to this there is one ultraviolet-C band resistant lamp cords 708 with a male female locking rubber water tight connection end 740. Said connection 740 will connect to the opposite end of the ultraviolet-C band resistant lamp cords 708 from which the water tight four pin locking connection 730 (shown in FIG. 16) is that will connect directly to the high output ultraviolet-C band lamps 900 (shown in FIG. 15). Said device 704 will be connected to the data collection terminal 1045 (shown in FIG. 4) for reporting of all data.

Figure 13:
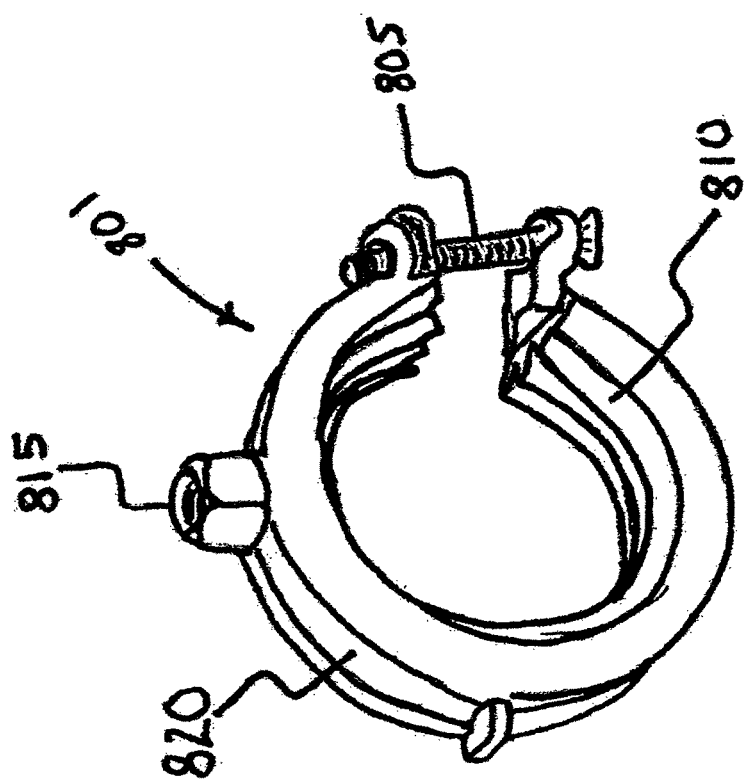
FIG. 13 is a perspective view of the ultraviolet-C band lamp clip with rubber grommet shock absorbing pads of the present invention.

FIG. 13 shows one embodiment of the Rapid Disinfection System 10 locking lamp clip with rubber grommet shock absorbing pads 801. Said device 801 is generally equipped with one flexible rubber grommet that encircles the entire Teflon coated glass tube 904 (shown in FIG. 15) of the high output ultraviolet-C band lamps 900 (shown in FIG. 15). In addition to this generally there is a locking set screw to tighten the said lamp clip 801 to the said lamp 900 (shown in FIG. 15). Said clip 801 has a hard surface band 820 that encompasses the entire assemble that holds the rubber grommet 810 in place. In addition to this band 820 there is a nut connected at the top for bolting this entire assembly directly to the protruding bolts 634 (shown in FIG. 18) from the reflective hard surface base portion of fixture 604 (shown in FIG. 18).

Figure 14:
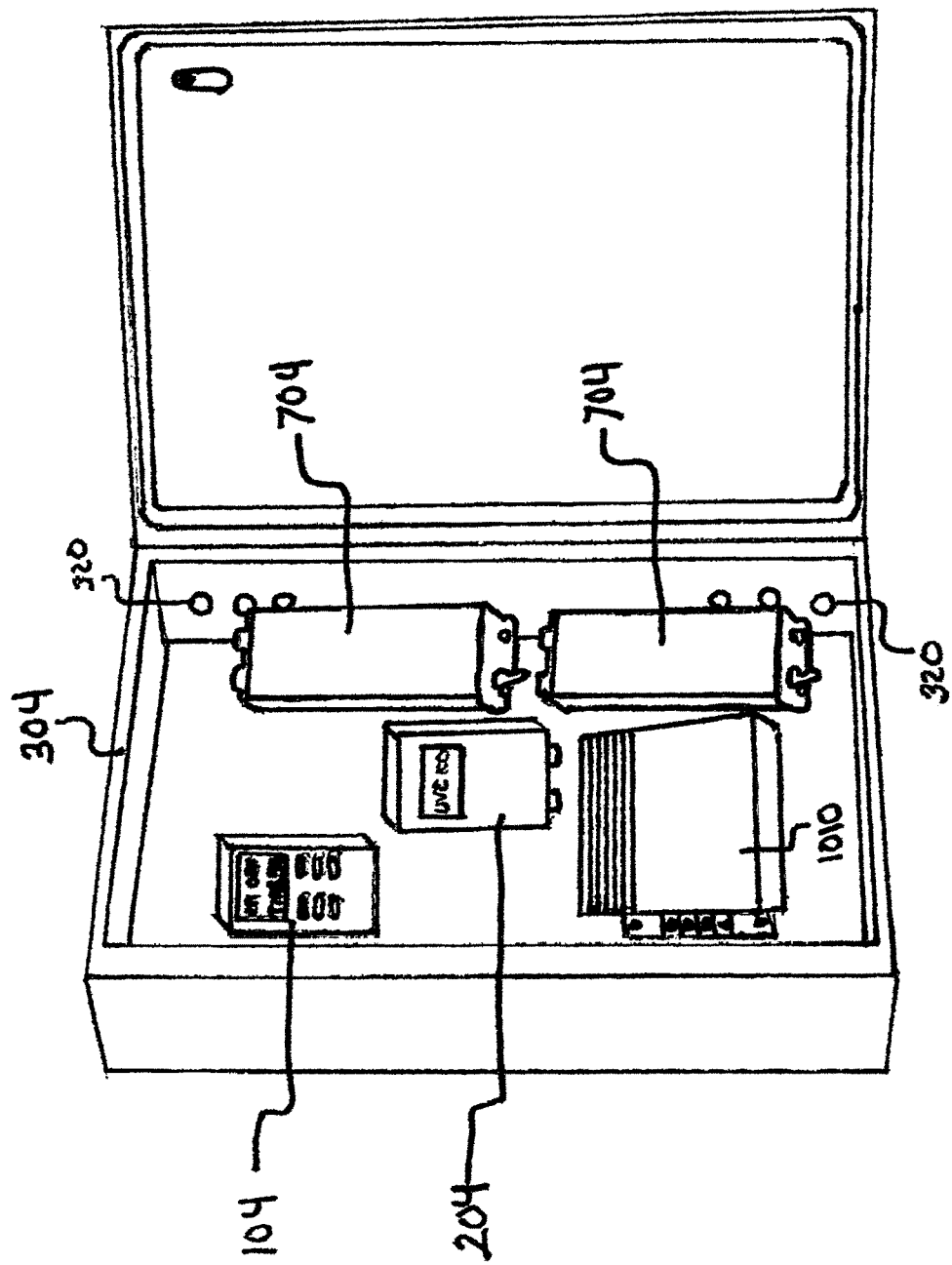
FIG. 14 is a perspective view of an embodiment of electronic components in the protective NEMA 4 weather tight cabinet of the present invention.

FIG. 14 shows one embodiment of the Rapid Disinfection System 10 locking NEMA 4 weather tight cabinet 304 generally enclosing the electrical components to operate the said system 10. All components shown in FIG. 14 are non-limiting examples of what may be housed in said cabinet 304. As shown on side panel of said cabinet 304 are at least 6 electrical knock out ports 320 to allow for electrical lines to come and go from within the cabinet 304. The electrical devices generally includes but are not limited to electrical devices mounted within the said cabinet 304 and said cabinet 304 is subsequently mounted within an exterior cabinet of the rescue ambulance. Such electrical devices may include Alternating Current (AC) Direct Current (DC) power inverter 1010, preset multifunction timer switch with manual override timer and auto shut off capabilities 104, ultraviolet-C band irradiance Intensity Monitor 204, and high output milliamp power supplies 704. Each of the said components may be mounted within the locking NEMA 4 weather tight cabinet 304 that will be mounted within the exterior cabinet of the rescue unit. Generally all of said devices will be connected to the data collection terminal 1045 (shown in FIG. 4) for reporting of all data.

Figure 15:
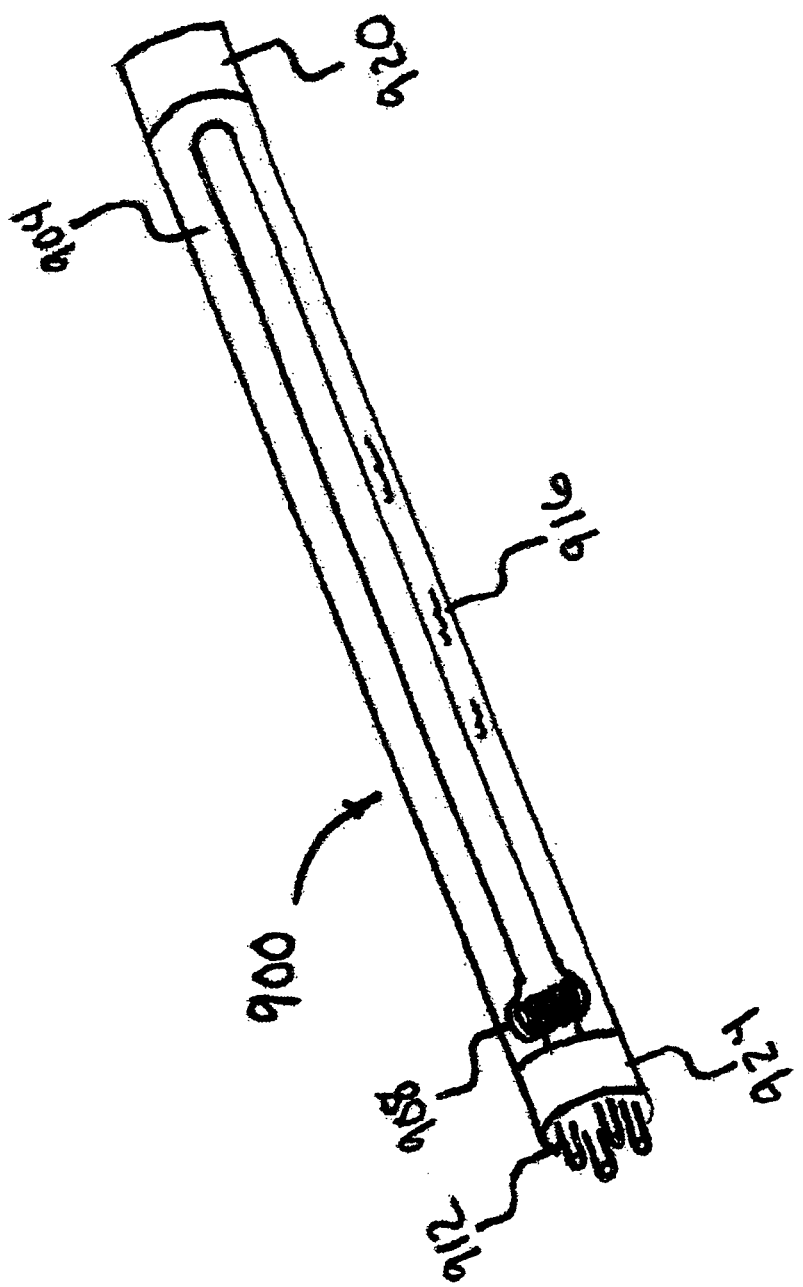
FIG. 15 is a perspective view of the high output ultraviolet-C band lamps of the present invention.

FIG. 15 shows one embodiment of the Rapid Disinfection System 10 high output ultraviolet-C band lamps 900. Generally said lamp 900 is hot start filament 908; with mercury vapor gas 916 within the hard quartz Teflon coated glass tube enclosure 904. Generally one end of said lamp 900 will be a solid molded composite cap 920. This said cap 920 is used to securely fasten said lamp 900 to reflective hard surface UVC Lamp mounting fixture 600 (shown in FIG. 18) with ultraviolet-C band lamp clip with rubber grommet shock absorbing pads 801 (shown in FIG. 13). In addition to this located at the opposite end of said lamp 900 is a solid molded composite cap 924 with four pin electrical connectors 912 used to connect to the ultraviolet-C band resistant lamp cords 708 (shown in FIG. 12) via the water tight four pin locking connection 730 (shown in FIG. 12). Generally the start and stop operation data of said lamp 900 will be collected by the data collection terminal 1045 (shown in FIG. 4) for reporting of all data.

Figure 16:
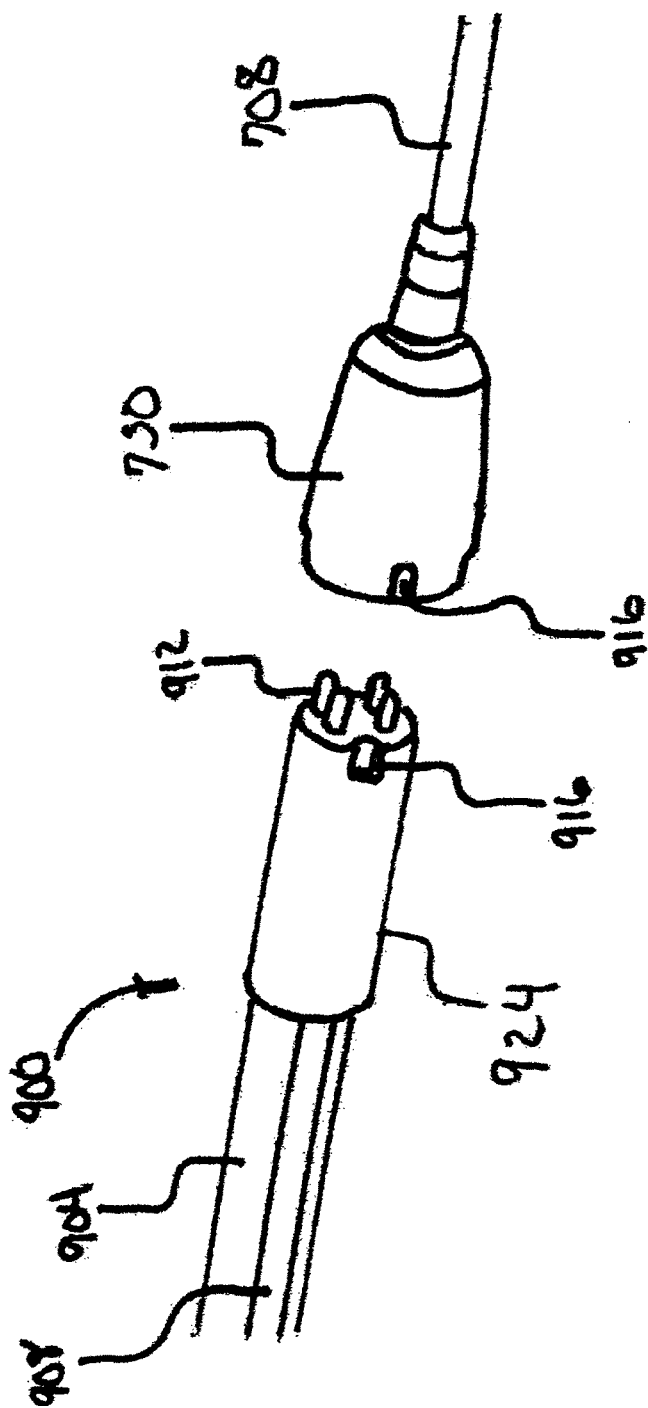
FIG. 16 is a perspective view of the high output ultraviolet-C band lamps and ultraviolet-C band resistant lamp cords of of the present invention.

FIG. 16 shows one additional embodiment of the Rapid Disinfection System 10 high output ultraviolet-C band lamps 900. In addition to the said lamp 900 is a locking connection knock out 916 located on the solid molded composite cap 924. In addition to this is a corresponding connection knock out 916 located water tight four pin locking connection 730. Said water tight four pin locking connection 730 is located at the lamp end of ultraviolet-C band resistant lamp cords 708.

Figure 17:
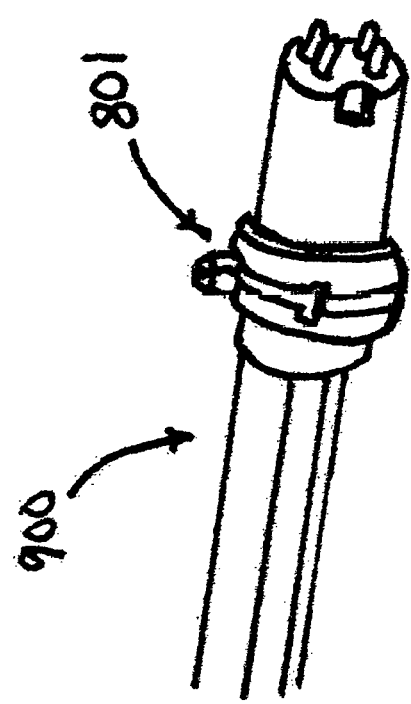
FIG. 17 is a perspective view of the high output ultraviolet-C band lamps and ultraviolet-C band lamp clip with rubber grommet shock absorbing pads of the present invention.

FIG. 17 shows one additional embodiment of the Rapid Disinfection System 10 showing the relationship between the locking lamp clip with rubber grommet shock absorbing pads 801 and high output ultraviolet-C band lamps 900

Figure 18:
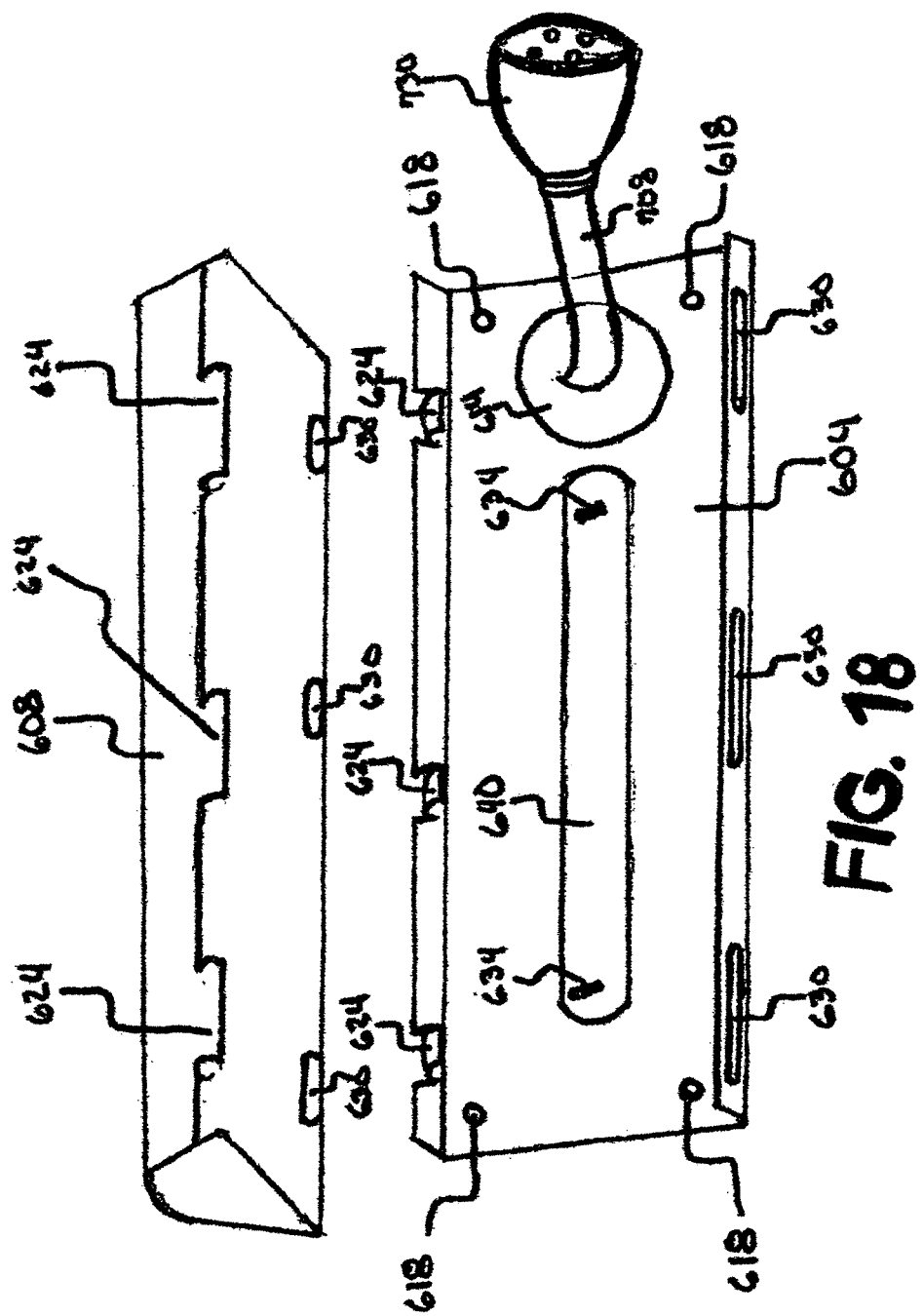
FIG. 18 is a perspective view of the reflective hard surface UVC Lamp mounting fixture base portion, safety cover and ultraviolet-C band resistant lamp cords of of the present invention.

FIG. 18 shows one additional embodiment of the Rapid Disinfection System 10 reflective hard surface UVC Lamp mounting fixture 600. Said fixture 600 consists of generally a reflective hard surface base portion of fixture 604 along with a reflective hard surface fixture safety cover 608. The reflective hard surface base portion of fixture 604 generally consist of as many as four mounting holes 618 located generally at the outer ends of the said base fixture portion 604. Generally located at one end of said base fixture 604 is at least one larger round lamp cord access opening 614 in which the ultraviolet-C band resistant lamp cords 708 with water tight four pin locking connection 730 may be run up in to the ceiling to make a connection with the high output milliamp power supplies 704 (shown in FIG. 12) located in an exterior cabinet of the rescue ambulance.

In addition to the said base portion 604 are at least 3 loop connection tabs 624 on one side of said base 604. These said tabs 624 will loop in to the respective slot openings 630 located in the reflective hard surface fixture safety cover 608. In addition to the said base portion 604 are at least 3 slot openings 630 located on the opposite side of the said tabs 624 on said base 604. These said slot openings 630 will accept the loop connection tabs 624 in order to lock the reflective hard surface fixture safety cover 608 down on the reflective hard surface base portion of fixture 604 Said safety cover 608 once locked in to place will cover the entire said base portion 604 and therefore conceal the high output ultraviolet-C band lamps 900 (shown in FIG. 15) and ultraviolet-C band resistant lamp cords 708.

Figure 19:
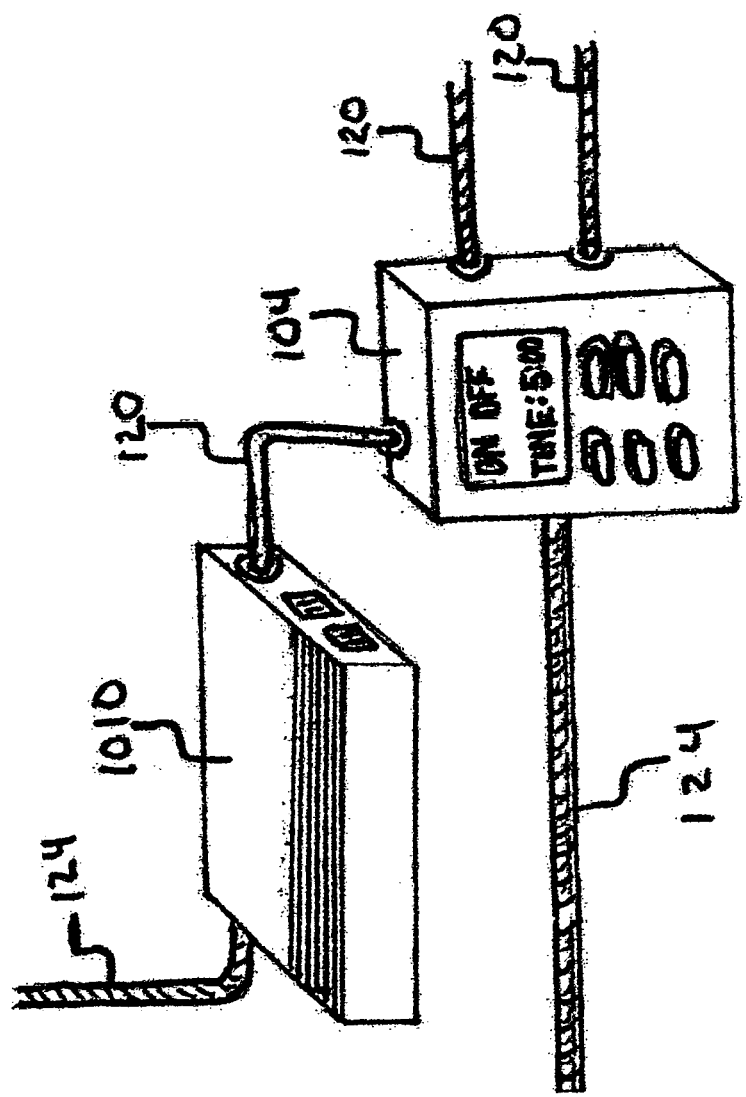
FIG. 19 is a perspective view of the Alternating Current (AC) Direct Current (DC) power inverter and preset multifunction timer switch with manual override timer and auto shut off capabilities of the present invention.

FIG. 19 shows one additional embodiment of the Rapid Disinfection System 10 Alternating Current (AC) Direct Current (DC) power inverter 1010. Said power inverter 1010 will be incoming hard wired 124 to the battery system (DC-Direct Current) of the rescue ambulance. The said power inverter will at the opposite side will be hard wire output 120 to the preset multifunction timer switch with manual override timer and auto shut off capabilities 104. In addition to this the said timer 104 will also have incoming hard wired 124 connected to the shore line power (AC-Alternating Current). Said timer 104 will then have out going power lines to feed electricity to the rest of the devices embodied in the Rapid Disinfection System 10. Thus, allowing for the Rapid Disinfection System 10 to operate in the rescue ambulance on AC power while parked in the emergency services facility or on DC battery power while on the road away from the emergency services facility. Generally, all of said devices will be connected to the data collection terminal 1045 (shown in FIG. 4) for reporting of all data.

Figure 20:
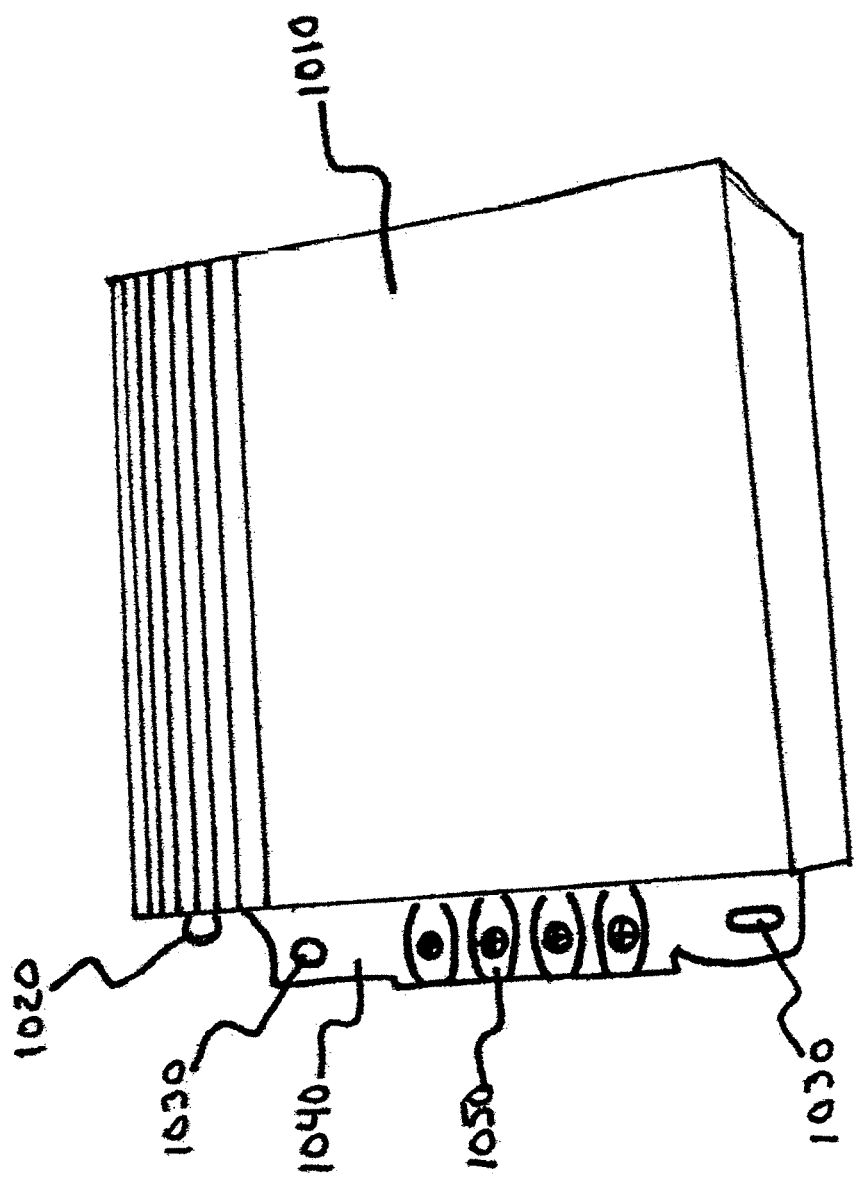
FIG. 20 is a perspective view of the Alternating Current (AC) Direct Current (DC) power inverter of the present invention.

FIG. 20 shows one additional embodiment of the Rapid Disinfection System 10 Alternating Current (AC) Direct Current (DC) power inverter 1010. Said power inverter 1010 will be mounted within locking NEMA 4 weather tight cabinet 304 (shown in FIG. 8*a*) and connected to the rescue ambulance battery. This connection will be terminated to the power terminals 1050 located on the mounting bracket 1040. Mounting screw holes are made available at each side of the power inverter 1010 to mount to the said cabinet 304 (shown in FIG. 8*a*). Said power inverter has one power indicator light 1020 to show that the system is operational. Said device 1010 will be connected to the data collection terminal 1045 (shown in FIG. 4) for reporting of all data.

FIG. 21*a* shows one additional embodiment of the Rapid Disinfection System 10 vibration resistant bolt assembly 1100. As shown the said bolt assembly 1100 consist of but not limited to one hard metallic screw 1130, one approximately one half inch rubber grommet washer 1120, one hard metallic toggle bolt 1110. As referred to in FIG. 21*a* the bolt assembly 1100 will utilize each mounting access hole 618 in the reflective hard surface base portion of fixture 604. As the said hard metallic screw 1130 is tightened to the said toggle bolt 1110 the wings of said toggle bolt 1110 will depress against the ceiling from above. With the bolt assembly 1100 tight, the one half inch rubber grommet washer 1120, will eliminate any vibrations caused by bumps while driving. Thus, the high output UVC lamps with reflective hard surface mounting fixtures 150 (shown in FIG. 2) will be securely fastened to the ceiling.

FIG. 21*b* shows one additional embodiment of the Rapid Disinfection System 10 vibration resistant bolt assembly 1100. This view is used to illustrate how the reflective hard surface base portion of fixture 604 will be securely fastened to the ceiling of the rescue ambulance patient cabin.

Although the invention has been described in terms of particular embodiments and applications, one of ordinary skill in the art, in light of this teaching, can generate additional embodiments and modifications without departing from the spirit of or exceeding the scope of the claimed invention. For example, the system of the present invention might be well-suited for applications outside of emergency services. Non-limiting examples include medical facilities, clean rooms, triage facilities and other athletic training rooms, military applications etc. Accordingly, it is to be understood that the drawings and descriptions herein are proffered by way of example to facilitate comprehension of the invention and should not be construed to limit the scope thereof.

The invention claimed is:

1. A Disinfection System, comprising:
a plurality of independent ultraviolet-C band lamps secured to the ceiling in a specifically calculated location within the rescue ambulance patient cabin; said ultraviolet-C band lamps will irradiate the interior of the said Rescue Ambulance Patient Cabin for a calculated time frame in order to achieve a three log reduction of colony forming units of a microorganism; will be achieved with a measured UV dose of 46,000 microwatts; wherein each of said ultraviolet-C band lamps is held in place by a mounting fixture;
each mounting fixture is comprised of a base portion that is used to connect the base portion of fixture to the ceiling of patient cabin of rescue ambulance; the base portion of fixture securing the ultraviolet-C band lamps thus suspending said lamps above the patient cabin surfaces to be disinfected; a safety cover that envelopes the entire base assembly and ultraviolet-C band lamp and protects the assembly and lamp from being damaged by any item knocking into the lamp.

2. The Disinfection System of claim 1 further comprising:
said base portion of mounting fixture will have access opening for ultraviolet-C band resistant lamp cords; a plurality of access holes for mounting bolt assemble connection to ceiling.

3. The Disinfection System of claim 1 further comprising:
a base portion of the mounting fixture has ultraviolet-C band lamp clips connected to the base portion of fixture at each end to securely fasten the ultraviolet-C band lamp in place.

4. The Disinfection System of claim 1 further comprising:
a fixture safety cover with port openings to connect with base portion of mounting fixture on one side and locking clips to securely lock in place said fixture safety cover located on the opposite side of the fixture safety cover.

5. The Disinfection System of claim 1 further comprising:
a first safety feature capable of shutting off each of a plurality of independent ultraviolet-C band lamps installed in a specifically calculated predetermined location within the patient cabin; wherein said safety feature comprises of a hard wired infrared motion and heat sensor detecting any motion or body heat within said patient cabin.

6. The Disinfection System of claim 5 further comprising:
the first safety feature comprises of a door interlock safety switch wherein the said door interlock safety switches detect if any of the patient cabin doors are ajar or in the unlatched position.

7. The Disinfection System of claim 1 further comprising:
a second safety feature capable of monitoring ultraviolet-C band irradiance intensity for end of life degradation.

8. The Disinfection System of claim 7 further comprising:
a third safety feature capable of sending warning audible notice of unsafe ultraviolet-C band irradiance intensity levels wherein said safety feature comprises of at least one ultraviolet-C band irradiance Intensity monitor with a UV sensor located within the rescue ambulance patient cabin wherein said ultraviolet-C band irradiance Intensity monitor with a UV sensor will be able to determine the ultraviolet-C band intensity output of the said ultraviolet-C band lamps.

9. The Disinfection System of claim 7 further comprising:
said ultraviolet-C band irradiance Intensity Monitor will detect if the ultraviolet-C band irradiance levels are above minimum safe operating level wherein the sensor will produce the following warnings but are not limited to a visual display, audible sound warning and will be able to communicate via blue tooth, wireless internet and or hard wire cabling to a manned monitoring station.

10. A Disinfection System, comprising:
an Alternating Current (AC) Direct Current (DC) power inverter; a timer switch to turn on the Disinfection System wherein said Alternating Current Direct Current power inverter for any 12 volt to 24 volt direct current draw from battery power source of rescue ambulance to 120 volt alternating current for energizing Rapid Disinfection System; wherein the Disinfection System can operate while in motion and no longer connected to shoreline power source, the rescue ambulance may energize the said Disinfection System while on the roadways; allowing for the said System to achieve a three log reduction of CFU's of microorganisms while away from shore line power source.

11. The Disinfection System of claim 10 further comprising:
a timer switch hard wired to the power inverter to allow for 24 volt battery power, additionally connected to shore line 120 volt power supply.

12. The Disinfection System of claim 10 further comprising:
a preset multifunction timer switch with manual override timer and auto shut off capabilities, wherein, a timer switch will be capable of turning on or off the said Disinfection System and allow for specific run time operation of said Disinfection System.

13. The Disinfection System of claim 10 further comprising:
a timer switch with preset function button that can be set for specific times of irradiance; a manual override switch that can run the system until the operator determines the shut off time.

14. A Disinfection System, comprising:
a data collection and transmittal device wherein said data collection system will receive input signals from but not limited to the ultraviolet-C band lamps, motion sensor, door interlock safety switches, timer switches and ultraviolet-C band irradiance intensity monitor with UV sensor; said data input signals collected in part or in whole will allow for but not limited to the verification of the measured UV dosage to achieve the three log reduction of CFU's of microorganisms.

15. The Disinfection System of claim 14 further comprising:
said data collection and transmittal device can transmit data to a terminal, wireless device, manned monitoring station, and a communication device within said rescue ambulance monitoring systems.

16. The Disinfection System of claim 14 further comprising:
Wherein, data information received can be viewed at said manned monitoring stations but are not limited to laptop computer, desk top computer, communication device within said rescue ambulance monitoring systems and other mobile wireless devices.

17. The Disinfection System of claim 14 further comprising:
Wherein, real time monitoring of all data points during the operation of the said Disinfection System.

18. The Disinfection System of claim 14 further comprising:
Wherein, said real time monitoring will display any triggered alarm showing the device that triggered the alarm and forced a shutdown of said Disinfection System, wherein said real time monitoring will not be affected by a critical safety feature shut down of said Disinfection System, and all alarms and run time calculations will be available for display at any manned monitoring station.

* * * * *